United States Patent
Yamamura

(10) Patent No.: US 11,803,970 B2
(45) Date of Patent: Oct. 31, 2023

(54) IMAGE JUDGMENT DEVICE, IMAGE JUDGMENT METHOD, AND STORAGE MEDIUM

(71) Applicant: Konica Minolta, Inc., Tokyo (JP)

(72) Inventor: Takuya Yamamura, Mitaka (JP)

(73) Assignee: KONICA MINOLTA, INC., Tokyo (JP)

( * ) Notice: Subject to any disclaimer, the term of this patent is extended or adjusted under 35 U.S.C. 154(b) by 127 days.

(21) Appl. No.: 17/127,066

(22) Filed: Dec. 18, 2020

(65) Prior Publication Data

US 2021/0192731 A1 Jun. 24, 2021

(30) Foreign Application Priority Data

Dec. 23, 2019 (JP) ................................. 2019-231092

(51) Int. Cl.
*G06T 7/11* (2017.01)
*G06T 7/00* (2017.01)
(Continued)

(52) U.S. Cl.
CPC .............. *G06T 7/11* (2017.01); *A61B 6/5211* (2013.01); *G06T 7/0012* (2013.01); *G06T 7/73* (2017.01);
(Continued)

(58) Field of Classification Search
CPC ............ G06T 7/11; G06T 7/73; G06T 7/0012
See application file for complete search history.

(56) References Cited

U.S. PATENT DOCUMENTS 8,391,572 B2 * 3/2013 Morita ................... G06V 40/67
382/128
11,227,384 B2 * 1/2022 Kashyap ................ G16H 30/00
(Continued)

FOREIGN PATENT DOCUMENTS

CN 101150977 A * 3/2008 ......... A61B 1/00009
JP 2007105264 A 4/2007
(Continued)

OTHER PUBLICATIONS

Machine translation of CN-101150977-A (Year: 2008).*
(Continued)

*Primary Examiner* — John Villecco
*Assistant Examiner* — Courtney Joan Nelson
(74) *Attorney, Agent, or Firm* — LUCAS & MERCANTI, LLP

(57) ABSTRACT

Disclosed is an image judgment device including a hardware processor that functions as an image acquirer that acquires image data of a medical image that is obtained by radiographing of a part including a region to be diagnosed of a patient, a segmentation unit that extracts an anatomical structure from the medical image to generate an extracted image, an image converter that performs image conversion on the extracted image to generate a converted image; a feature value extractor that calculates a feature value from the extracted image and/or the converted image by using a result of machine learning; and a judgment unit that judges whether the medical image is taken with positioning appropriate for diagnosis based on the feature value by using a result of machine learning concerning feature values.

13 Claims, 11 Drawing Sheets

(51) Int. Cl.
*A61B 6/00* (2006.01)
*G06T 7/73* (2017.01)
*G06V 10/764* (2022.01)

(52) U.S. Cl.
CPC .. *G06V 10/764* (2022.01); *G06T 2207/20081* (2013.01); *G06T 2207/30008* (2013.01)

(56) References Cited

U.S. PATENT DOCUMENTS

| | | | | |
|---|---|---|---|---|
| 2002/0027970 | A1* | 3/2002 | Chapman | G01N 23/20 378/62 |
| 2007/0086641 | A1* | 4/2007 | Nakamura | G06T 7/0012 382/132 |
| 2014/0093153 | A1* | 4/2014 | Sofka | G06T 7/0014 382/131 |
| 2017/0365047 | A1* | 12/2017 | Bequé | G16H 40/63 |
| 2018/0144214 | A1* | 5/2018 | Hsieh | G06T 7/0002 |
| 2019/0147305 | A1* | 5/2019 | Lu | G06F 18/2413 382/157 |
| 2019/0228547 | A1* | 7/2019 | Chandarana | G06N 3/048 |
| 2019/0259493 | A1* | 8/2019 | Xu | G16H 30/40 |
| 2019/0287241 | A1 | 9/2019 | Hill et al. | |

FOREIGN PATENT DOCUMENTS

| | | |
|---|---|---|
| JP | 2010-051456 A | 3/2010 |
| JP | 2011-255061 A | 12/2011 |
| JP | 2019-035626 A | 3/2019 |
| JP | 2019093137 A | 6/2019 |

OTHER PUBLICATIONS

JPO, Office Action dated Jul. 11, 2023 issued in connection with the related Japanese Application No. 2019-231092, with machine English translation, 10 pages.

* cited by examiner

JUDGMENT TARGET IMAGE

SEGMENTED IMAGE OF JUDGMENT TARGET IMAGE

CLASSIFICATION RESULT
CLASS A: 5%
CLASS B: 10%
CLASS C: 85%

# IMAGE JUDGMENT DEVICE, IMAGE JUDGMENT METHOD, AND STORAGE MEDIUM

CROSS-REFERENCE TO RELATED APPLICATIONS

The entire disclosure of Japanese Patent Application No. 2019-231092 filed on Dec. 23, 2019 is incorporated herein by reference in its entirety.

BACKGROUND

Technological Field

The present invention relates to an image judgment device, an image judgment method, and a storage medium.

Description of the Related Art

Radiographic images using X-rays, etc. are taken in medical facilities such as hospitals. They are used to detect lesional tissues and abnormalities in various parts of human bodies in a non-erosive way for diagnosing diseases.

In imaging of radiographs, a region to be the target of diagnosis is sometimes out of range due to differences in posture, physique, or movement between individuals, as it is difficult to directly check the site to be imaged before imaging.

In cases where the image is improper, it is necessary to perform re-imaging at a later date if judgement of whether the image is taken properly is done in a later diagnosis. That may be a burden to the patient who undergoes the imaging test.

There have been devices that judge whether the positioning in imaging is proper or not by reading digital data of imaged radiographs.

For example, JP 2011-255061 A discloses a technique in which predetermined feature values are extracted from the image data of a part adjacent to a boundary of an irradiated field on a radiograph and whether a specific part is partially missing from the radiograph or not is judged on the basis of learning results of a predetermined algorithm.

JP 2010-051456 A also discloses a technique in which anatomical structures are extracted by analysis of a medical image and evaluation items of positioning in imaging of the medical image are evaluated on the basis of the results of extraction of the structures on a scale of points by item.

Further, though the field of application is different from that of the present invention, JP 2019-035626 A discloses a technique in which a convolutional neural network is used to judge the type and state of a tire from a tire image.

SUMMARY

However, in the technique of JP 2011-255061 A, a judgment of whether the medical image is appropriate for diagnosis is made on the basis of whether there is a part missing in a target region on the image.

In this respect, the medical image may be judged as inappropriate for diagnosis in cases other than where there is a part missing in a target region.

The machine learning is used in the judgment of whether a specific part is partially missing from a radiograph or not, but not used in extraction of feature values.

In the technique of JP 2010-051456 A, the feature values evaluated from the extraction results of the structures are preset by an intervening developer.

Thus, the analysis parameters are exclusive to individual cases, and cannot be robustly applied to various regions and patterns.

In the technique of JP 2019-035626 A, deep learning is adopted in the process, in which classification is directly done for images to be judged using the deep learning.

Thus, when a large amount of training data is prepared, it is possible to realize effective deep learning for extracting feature values and obtain judgment results with a high accuracy. However, when training data is scarce, it is impossible to properly extract features in deep learning, resulting in a judgment with a low accuracy.

In the field of medical imaging, it is difficult to collect a large amount of training data of each region of interest (an "anatomical structure," a part to be the basis for the judgement of whether the image is appropriate for diagnosis) in a human body. A structure that enables a judgement with a high accuracy is desired even when training data is scarce.

The present invention has been conceived in view of the above circumstances, and has an object of providing an image judgment device, an image judgment method, and a storage medium that can judge whether a medical image is taken with proper positioning with a higher accuracy.

To achieve at least one of the abovementioned objects, according to an aspect of the present invention, an image judgment device reflecting one aspect of the present invention includes: a hardware processor that functions as:

an image acquirer that acquires image data of a medical image that is obtained by radiographing of a part including a region to be diagnosed of a patient;

a segmentation unit that extracts an anatomical structure from the medical image to generate an extracted image;

an image converter that performs image conversion on the extracted image to generate a converted image;

a feature value extractor that calculates a feature value from the extracted image and/or the converted image by using a result of machine learning; and a judgment unit that automatically judges whether the medical image is taken with positioning appropriate for diagnosis based on the feature value by using a result of machine learning concerning feature values.

To achieve at least one of the abovementioned objects, according to another aspect of the present invention, an image judgment method reflecting one aspect of the present invention includes:

acquiring image data of medical images that are each obtained by radiographing of apart including a region to be diagnosed;

extracting an anatomical structure from each of the medical images to generate extracted images;

preparing training data by associating the extracted images respectively with adequacy classes of positioning in radiographing the corresponding medical images;

training a convolutional neural network with the training data so as to set a parameter of the convolutional neural network; and acquiring image data of a target medical image that is obtained by actual radiographing of a part including the region to be diagnosed of a patient;

extracting an anatomical structure from the target medical image to generate an extracted image; and inputting the extracted image to the convolutional neural network having the parameter set by the training, and thereby judging as to whether the target medical image was taken with positioning appropriate for diagnosis.

To achieve at least one of the abovementioned objects, according to another aspect of the present invention, a non-transitory recording medium reflecting one aspect of the present invention stores a computer readable program that causes a computer to:

acquire image data of a medical image that is obtained by radiographing of a part including a region to be diagnosed of a patient;

extract an anatomical structure from the medical image to generate an extracted image;

perform image conversion on the extracted image to generate a converted image;

calculate a feature value from the extracted image and/or the converted image by using a result of machine learning; and automatically judge whether the medical image is taken with positioning appropriate for diagnosis based on the feature value by using a result of machine learning concerning feature values.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention, wherein.

DETAILED DESCRIPTION OF THE EMBODIMENTS

Hereinafter, an embodiment of an image judgment device, an image judgment method, and a storage medium according to the present invention is described with reference to the drawings.

The embodiment hereinafter described includes technically preferable limitations for carrying out the present invention, which are not intended to limit the scope of the present invention to the embodiment and illustrated examples.

Figure 1:
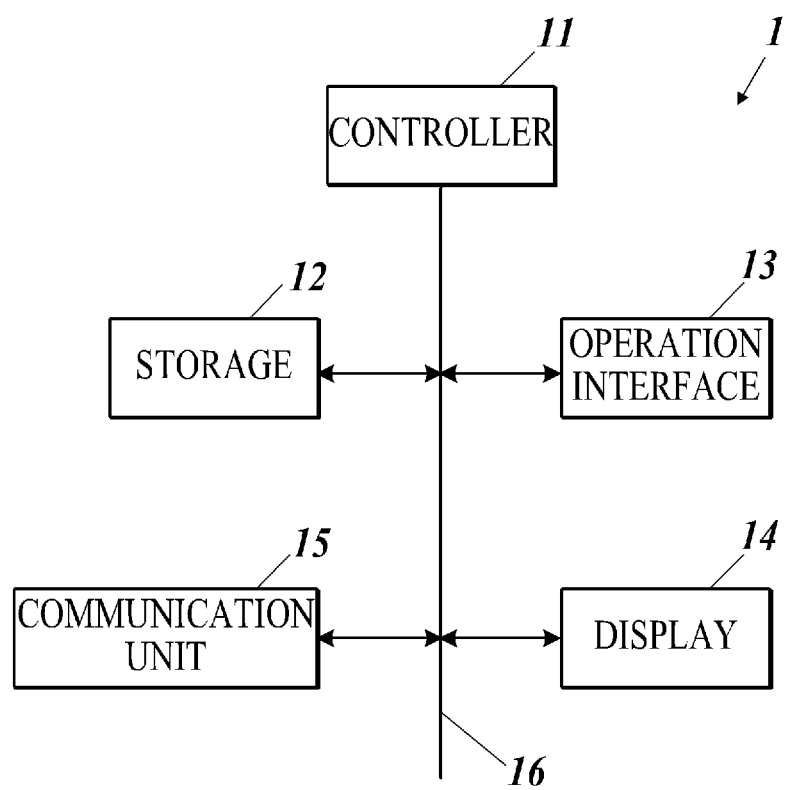
FIG. 1 is a block diagram of a main configuration of an image processing device as an image judgment device in an embodiment.

FIG. 1 is a block diagram of a main configuration of an image processing device in the present embodiment.

The image processing device 1 in the present invention functions as an image judgment device that acquires image data of a medical image(s) taken by radiographing of a part including a region of interest of a patient and that judges whether the medical image is taken with positioning appropriate for diagnosis.

In medical facilities such as hospitals, a lot of radiographs (medical images) including X-ray images are taken. The medical images are used to detect lesional tissues and abnormalities in various parts of a human body such as lungs and head in a non-erosive way for diagnosing diseases.

In taking such medical images, an operator of the imaging gives instructions from another room (anterior room, etc.) in order to prevent exposure. Thus, it is difficult to check the state (positioning, orientation, etc.) of an imaging target region right before the imaging. A caretaker cannot accompany the patient for the same reason. Thus, in some cases, the region to be diagnosed is not normally imaged as the patient to be imaged may not maintain an appropriate posture or may move before the imaging. The imaging results may significantly differ due to individual differences in physique, etc., even when the imaging is done in the same way.

Especially, in imaging of a limb such as a lateral knee, the imaging results significantly differ depending on the incident angle of radiation (X-ray), the tilting of the target region of the patient, etc. This makes the positioning difficult in the imaging, and increases the possibility of an imaging failure (failure in imaging) that requires reimaging.

It is burdensome to require the subject patient to come back at a later date if reimaging is necessary. Thus, whether reimaging is necessary or not is preferably checked right after the imaging.

Figure 2A:
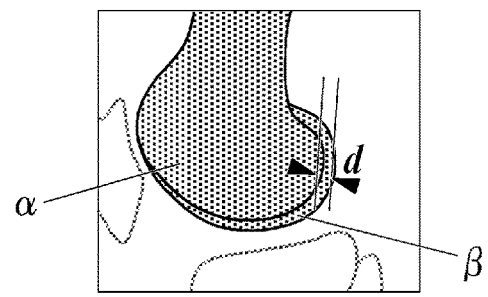
FIG. 2A is a schematic diagram showing an anatomical structure on a lateral image of the knee.

The judgement of an imaging failure differs depending on the target of diagnosis. For example, the adequacy of a lateral image of the knee is judged using a non-overlapping portion (a width of a non-overlapping portion, a non-overlapping amount d) between a medical condyle α and a lateral condyle β as shown in FIG. 2A. Commonly, an imaging failure is judged by the non-overlapping portion (the non-overlapping amount d) between the medial condyle α and the lateral condyle β of 7 mm or more.

Figure 2B:
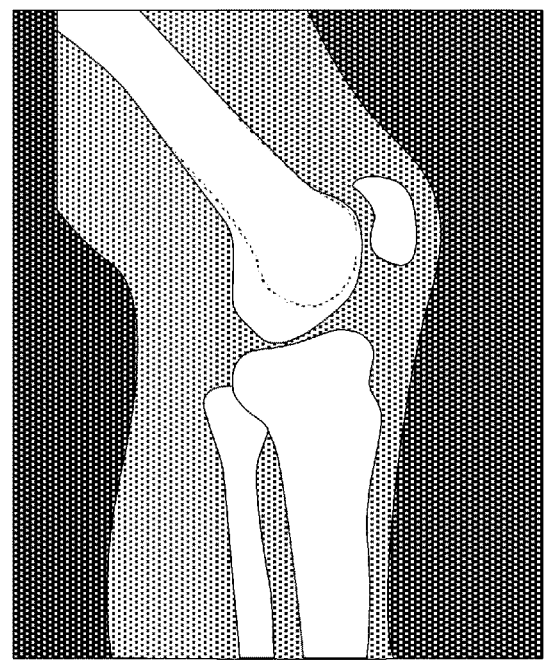
FIG. 2B is an example of a lateral image of the knee taken with proper positioning.
Figure 2C:
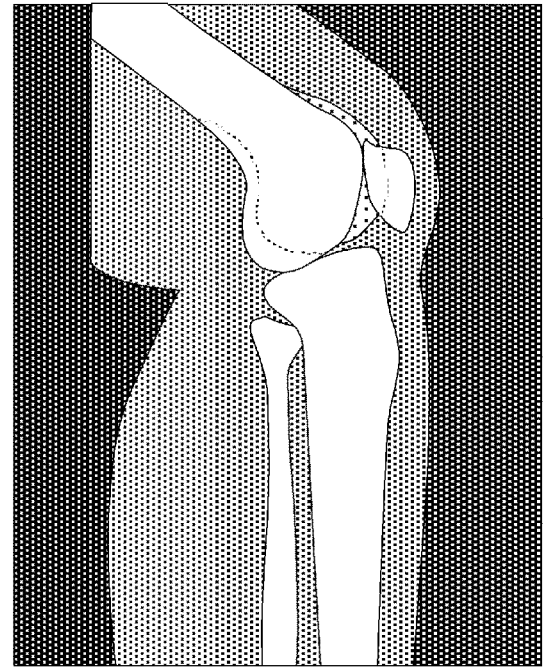
FIG. 2C is an example of a lateral image of the knee taken with improper positioning.

FIG. 2B shows an example of a proper lateral image of the knee in the above condition. FIG. 2C shows an example of an improper lateral image of the knee in the above condition.

However, whether an imaging failure requires re-imaging is not clear on the image, and the judgment is difficult.

Therefore, the image processing device 1 in the present invention uses machine learning in the judgement of whether the image is taken with positioning appropriate for diagnosis, enabling the judgement with a high accuracy.

As shown in FIG. 1, the image processing device 1 in the present embodiment includes a controller 11 (hardware processor), a storage 12, an operation interface 13, a display 14, and a communication unit 15, and those components are connected with each other via a bus 16.

The controller 11 (hardware processor) is a computer composed of a central processing unit (CPU), a random access memory (RAM), etc.

The CPU of the controller 11 reads out a system program and various processing programs stored in the storage 12 (for example, a memory for storing programs), develops them in a working area of the RAM, executes various kinds of processing such as image processing described later according to the developed programs, and centrally controls operations of the components of the image processing device 1, according to the user operation via the operation interface 13. The CPU receives signals and data and sends control signals and commands via the bus 16 to and from the other components.

In this embodiment, the controller 11 (hardware processor) functions as: an image acquirer that acquires image data of a medical image that is obtained by radiographing of a part including a region to be diagnosed of a patient; a segmentation unit that extracts an anatomical structure from the medical image to generate an extracted image; an image converter that performs image conversion on the extracted image to generate a converted image (an imaging processor that performs processing such as image conversion to generate a processed image); a feature value extractor that calculates a feature value from the extracted image and/or the converted image by using a result of machine learning; and a judgment unit that automatically judges whether the medical image is taken with positioning appropriate for diagnosis based on the feature value by using a result of machine learning concerning feature values.

The functions of the controller 11 described above are realized by the CPU of the controller 11 in cooperation with the programs stored in the storage 12.

The functions are described later in detail.

The storage 12 includes a non-volatile semiconductor memory such as a solid state drive (SSD) and a hard disk drive (HDD). The storage 12 may include a removable flash memory.

The storage 12 stores various programs such as ones for executing various kinds of image processing by the controller 11, parameters necessary for executing the processing by the programs, data such as processing results, etc. The programs stored in the storage 12 are stored in the form of computer readable program code, and the controller 11 executes the operations in accordance with the program code.

In this embodiment, a program for judging the positioning concerning medical images is stored in the storage 12, the controller 11 performs an image judgment process including a positioning judgment process according to the program.

The storage 12 in this embodiment stores various kinds of training data (for example, a training data group 12a for segmentation in FIG. 6 and a training data group 12b for classification in FIG. 8) which is referred to in machine learning.

The operation interface 13 includes a keyboard including cursor keys, number input keys, and various function keys, and a pointing device such as a mouse, and outputs command signals input by user operation on the keyboard or mouse to the controller 11. The operation interface 13 may include a touch panel on a display screen of the display 14, and in that case, the command signals input via the touch panel are output to the controller 11.

The display 14 is composed of a monitor such as a liquid crystal display (LCD) and a cathode ray tube (CRT), for example.

Figure 9:
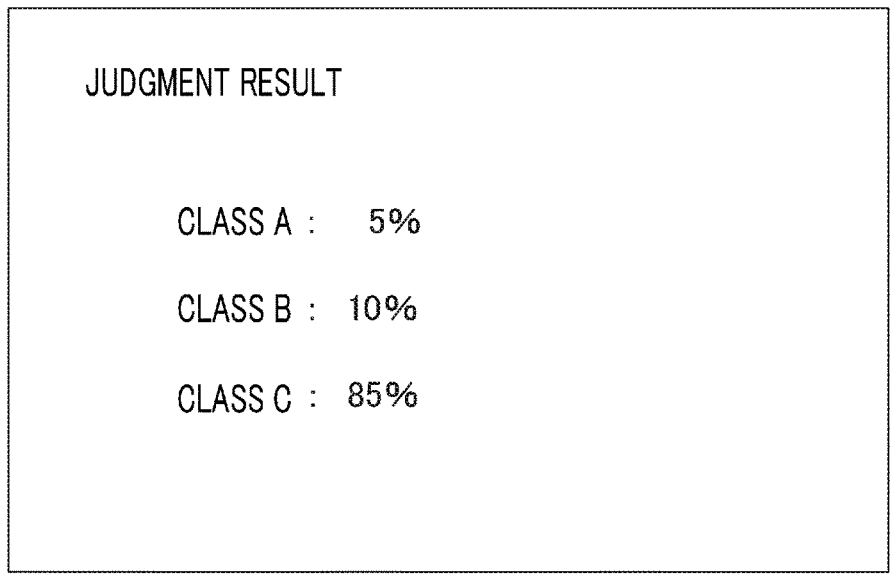
FIG. 9 shows an example of a result display screen of the positioning judgment process.
Figure 10:
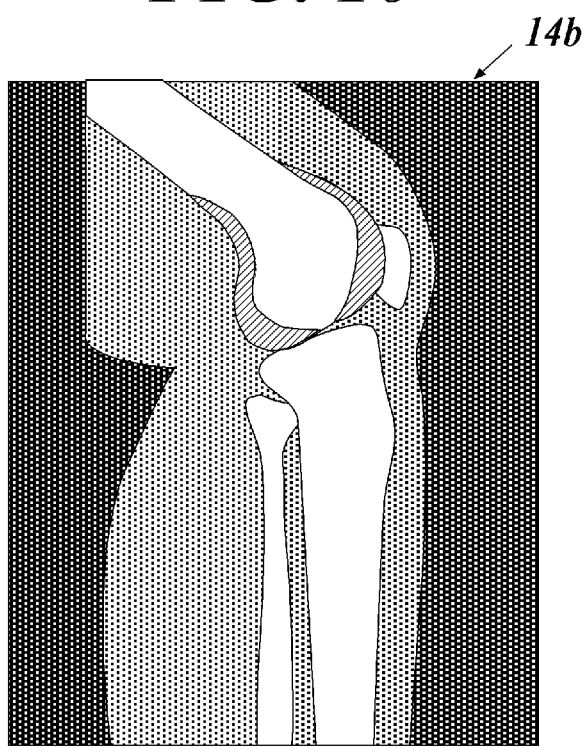
FIG. 10 shows an example of a segmentation display screen for displaying a segmentation result image.

The display 14 displays screens of various images and data such as related information (for example, a result display screen 14a of the positioning judgment process as shown in FIG. 9 and a segmentation display screen 14b as shown in FIG. 10) according to the command of the signals input from the controller 11.

The communication unit 15, which includes a LAN adapter, a modem, and a TA, controls data communication between the devices on the communication network. The communication unit 15 may include a communication interface such as a network card, for example.

Though not shown in the drawings, a hospital information system (HIS), a radiology information system (RIS), a picture archiving and communication system (PACS), etc. are connected to the image processing device 1 in this embodiment.

The communication unit 15 can send and receive various kinds of data to and from an external device(s), and for example, image data taken with an external imaging device (medical radiograph data) is input to the image processing device 1 via the communication unit 15. The storage 12 stores the input image data, etc. as necessary.

Next described is the operation of the image judgment process including the positioning judgment process in this embodiment.

Figure 3:
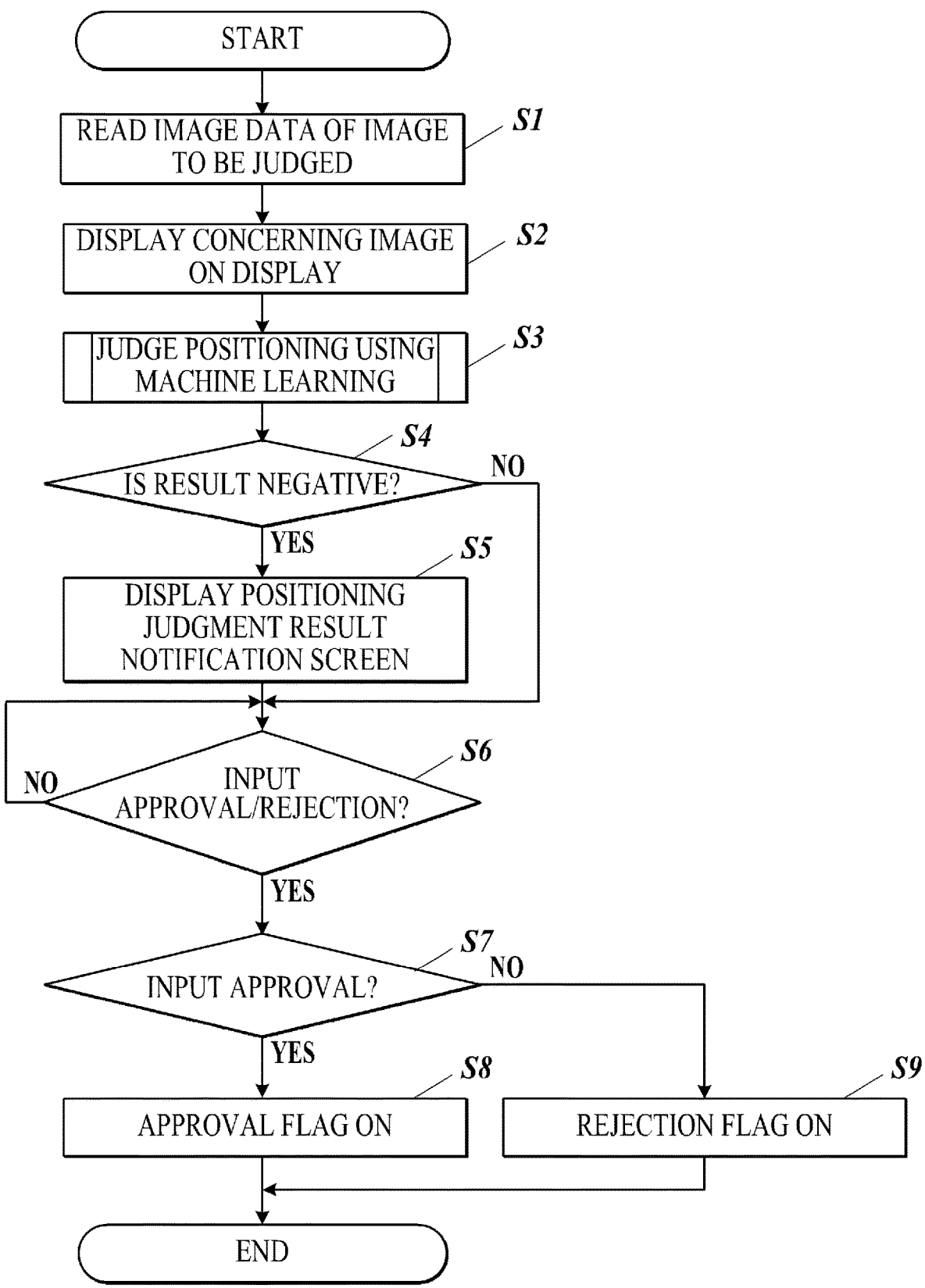
FIG. 3 is a flowchart showing an image judgment process according to the embodiment.

FIG. 3 is a flowchart showing control steps of the image judgment process by the controller 11 (the CPU of the controller 11, etc.). The image judgment process is started by an input signal based on a user's operation to command start via the operation interface 13.

As shown in FIG. 3, when the image judgment process is started, the CPU of the controller 11 first reads image data of a medical image (image data of a medical image obtained in actual imaging to be a target of the judgment) obtained by radiographing of a part including a diagnosis target region of a patient from the storage 12 (Step S1).

In this embodiment, the image data, on which initial corrections such as brightness and contrast adjustments are done after being imaged by the radiographic imaging apparatus, etc., is stored in the storage 12. The image data input to the controller 11 is not particularly limited. The data may not have undergone any correction processing, or may have undergone correction processing such as grid correction and gain correction, gradation processing, dynamic range compression processing, or enhancement processing such as edge enhancement. The image data may have undergone various kinds of interpolation such as reduction processing and rotation and geometric transformation. The image data may be obtained by "pre-exposure" (radiation exposure at a low dose before an image to be actually used for diagnosis is obtained). The image data may involve an image among a series of still images continuously taken, or a part cut out from dynamic data.

When the target image data is read, the CPU of the controller 11 displays the medical image based on the image data with related information, an operation menu, etc. on the display 14 (Step S2). It is not essential to display the image on the display 14.

The CPU of the controller 11 performs the positioning judgment process in which whether the read image data involves a medical image of a specific part of the subject body (the diagnosis target of the patient) taken with positioning appropriate for diagnosis is judged (Step S3).

In this embodiment, machine learning is used in the positioning judgment process by the CPU (the controller 11).

The positioning judgment process (Step S3 in FIG. 3) is described here in detail with reference to FIGS. 4 to 8.

Figure 4:
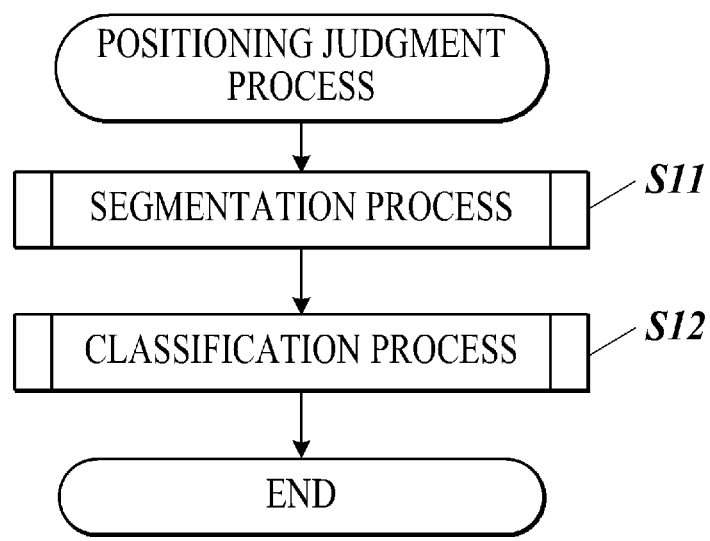
FIG. 4 is a flowchart showing a positioning judgment process using machine learning shown in FIG. 3.

FIG. 4 is a flowchart showing the positioning judgment process.

As shown in FIG. 4, in the positioning judgment process, a segmentation process (Step S1) is performed, and then a classification process (Step S12) is performed on the basis of the result of the segmentation process (Step S11).

The segmentation process for image data is broadly defined as division of an image, but in this embodiment, it is defined as extraction of a region to be focused on from a whole image, or especially, generation of an extracted image (segmentation result image) on which an "anatomical structure" to be focused on (referenced) in the judgment of adequacy of positioning is extracted from the medical image acquired by the controller 11.

The "anatomical structure" to be the target of extraction here differs between medical images to be the target of judgement of adequacy of positioning. For example, the "anatomical structure" is a medial condyle α, a lateral condyle β, or a non-overlapping portion between the medical condyle α and the lateral condyle β (a width of a non-overlapping portion, a non-overlapping amount d as shown in FIG. 2A) on a lateral image of the knee.

In this embodiment, the "anatomical structure" to be focused on in the judgement of adequacy of positioning (that is, the target of extraction) is the non-overlapping portion between the medial condyle α and the lateral condyle β, for example.

The "anatomical structure" to be the target of extraction differs depending on the image type, target, etc.

The segmentation process includes various methods, and any method can be used.

For example, in the segmentation process using an algorithm using the Otsu binarization, an image is divided into areas by a predetermined threshold value of pixel.

However, in a binarization method, the accuracy depends on the contrast of the image, and the segmentation may be impossible in the case where images taken under different conditions are input. The condition is, for example, the tube voltage in radiographing, or the thickness of a patient's body.

In this regard, the segmentation may be more accurately performed by, for example, a method called "snakes" using active contours for segmenting images, a level set method expressing inside and outside areas with the level set function, or a method using deep learning than by a binarization method.

With deep learning, especially, the segmentation process can be performed based on results of learning that uses the contrast of the image, etc. That is preferable because the segmentation process more robust can be expected.

The segmentation process for image data to be used may be instance-aware segmentation that distinguishes individual objects or semantic segmentation that does not distinguish individual objects in identical classes.

In the embodiment hereinafter described, the semantic segmentation is applied, in which semantics of pixels are each predicted and analyzed, for example. In the semantic segmentation, all the pixels on the image are classified by pixel (each pixel) for segmentation and extraction.

Neural networks specialized in the segmentation of images (semantic segmentation) (hereinafter also referred to as "network") are, for example, Seg-Net and U-Net. Those two networks, which use a convolutional neural network (CNN) and have mechanisms of both encoder and decoder, perform the segmentation process to divide an image into sets of pixels with semantics.

The neural network used for the segmentation process is not limited to Seg-Net or U-Net, and various networks may be appropriately used.

Figure 5:
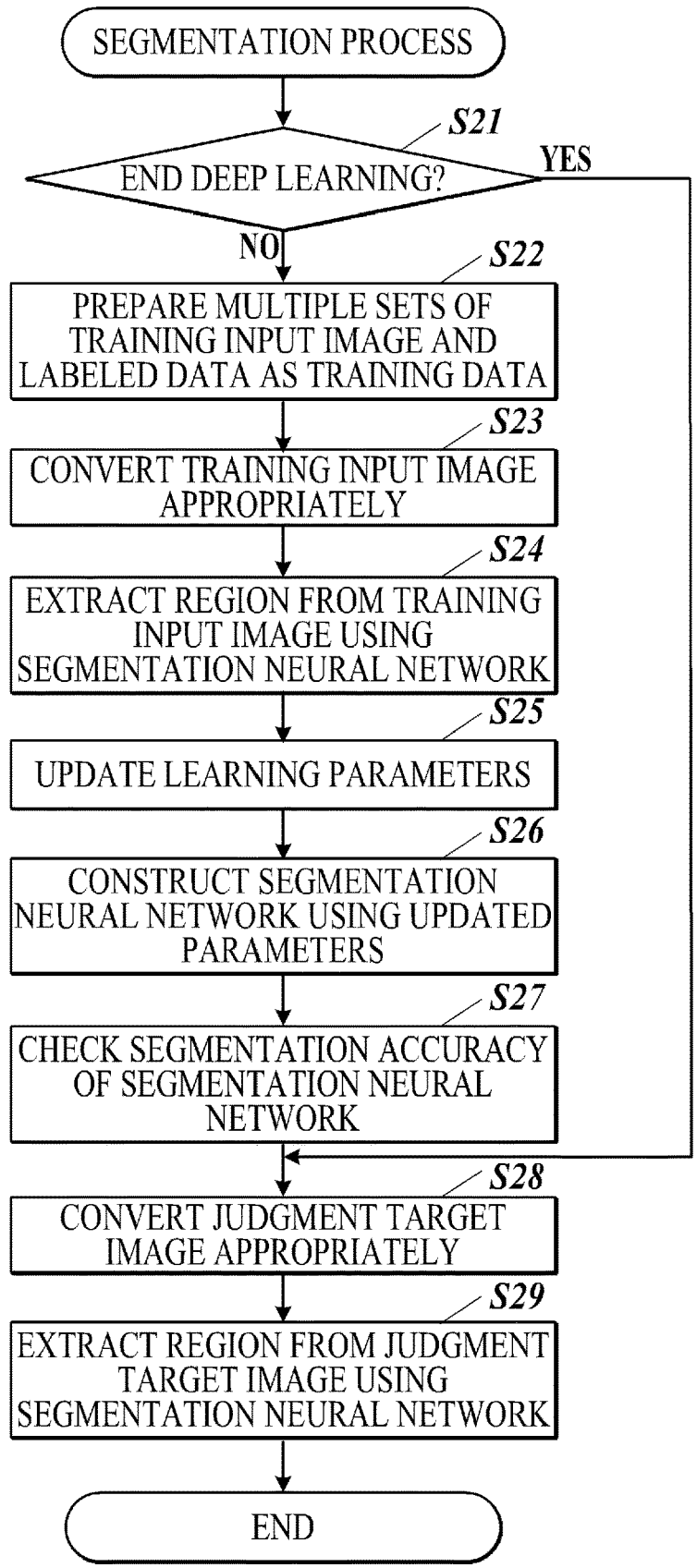
FIG. 5 is a flowchart showing a segmentation process shown in FIG. 4 in detail.

FIG. 5 is a flowchart showing the segmentation process in this embodiment. In FIG. 5, the segmentation process is performed using deep learning (semantic segmentation).

A neural network for processing is constructed by deep learning beforehand so as to use a method involving the deep learning in the segmentation process.

In this embodiment, when the image data of the judgment target is input, the controller 11 determines whether the deep learning is completed (Step S21). If the deep learning is not sufficient (Step S21; NO), multiple sets of training data are prepared (Step S22), and the storage 12, for example, stores the multiple sets of training data (see the training data group 12*a* in FIG. 6).

Figure 6:
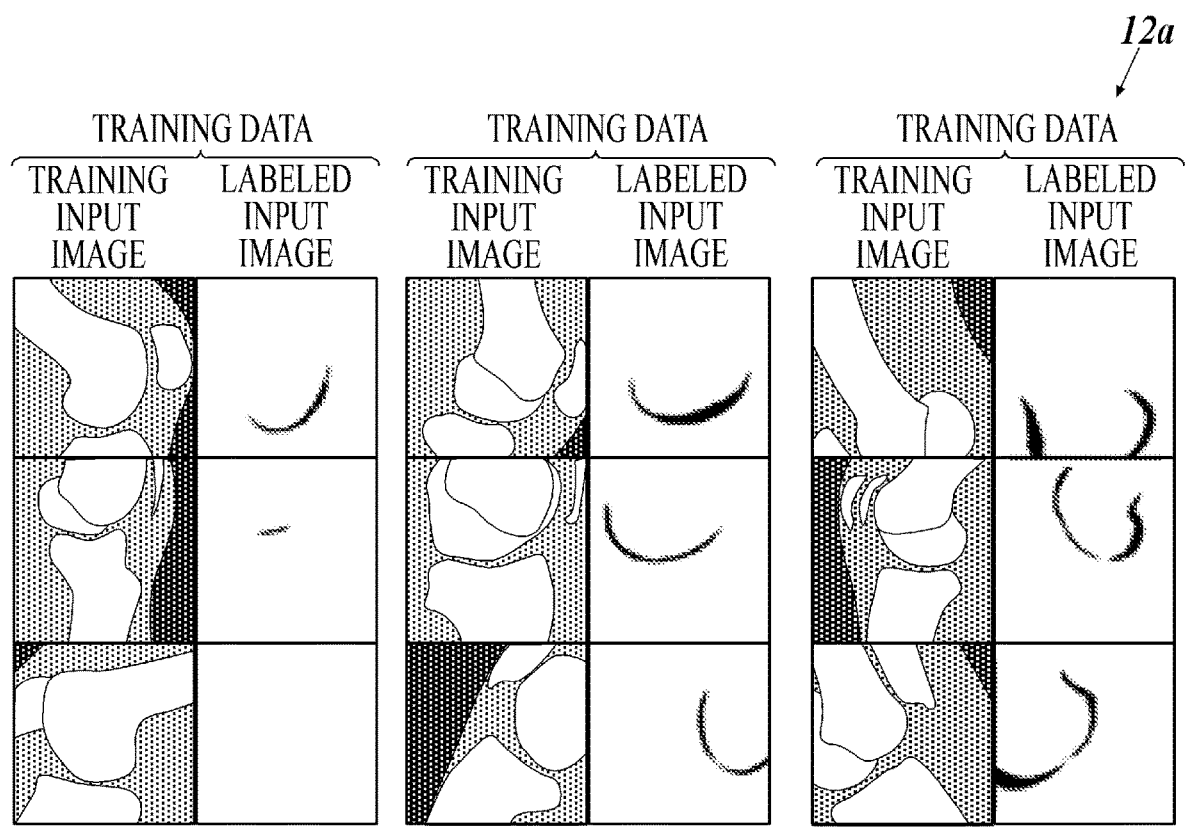
FIG. 6 shows an example of a training data group used in construction of a neural network for segmentation.

FIG. 6 shows an example of a training data group stored in the storage.

As shown in FIG. 6, the training data group 12*a* includes sets of a training input image (data of an input image for training) and labeled data (data of a labeled image as a result of segmentation) of an extracted image of an "anatomical structure" such as a non-overlapping portion of the medial condyle α and the lateral condyle β which is correctly extracted from the input image.

As more sets of the training data are prepared in the training data group 12*a*, the effect of the deep learning is enhanced and the accuracy of the constructed neural network is improved. The sets of training data (training input images in the training data) in the training data group 12*a* preferably include image data obtained in different conditions of, for example, the radiation amount in imaging, the incident angle of radiation, etc. of patients different in sex, age, physique, etc. As images taken in various conditions are used, a neural network more robust that can deal with various input images is expected to be constructed.

In the segmentation process, various kinds of image conversion (step S23) is performed as needed before the extraction of region for reduction of unnecessary noise, shortening of calculation time, etc.

An example of the image conversion is trimming. As for trimming, a region of interest (for example, around knee joints including the medial condyle α and the lateral condyle β) is trimmed from the original image, and the segmentation process is performed on the trimmed image (converted image). The trimming method is not limited, and a region of interest may be manually set, or automatically set to be trimmed.

Next, the prepared multiple sets of training data are learned using a convolutional neural network, and parameters for the convolutional neural network are set.

Specifically, the semantic segmentation is performed on images as follows: the neural network for segmentation is applied to the original training input images or the converted training input images; and at least part of pixels are associated with one or more semantic predictions. This is how the extraction of desired regions from images is performed (Step S24), and the extracted image (segmentation result image) is generated.

Then, the controller 11 updates the learning parameters as necessary (Step S25), and constructs a segmentation neural network (neural network for segmentation) using the updated parameters (Step S26).

The controller 11 tests whether correct answer data (data of the segmentation result image on which an "anatomical structure" is extracted) can be acquired from an input image using a set of input image data and labeled data prepared for testing, and checks the segmentation accuracy of the segmentation neural network after learning (Step S27).

If the accuracy is insufficient, the structure of the network is changed (for example, the number of the convolutional layers is changed (increased or decreased), the type of the network to be applied is changed, etc.), the parameters are modified, or more training data is learned.

On contrary, if the controller 11 determines that the deep learning is sufficient (Step S21; YES), the target image is converted as needed (Step S28), and an "anatomical structure" is extracted (Step S29) to generate an extracted image (segmentation result image), by applying the learned neural network for segmentation to the original target image or the converted target image.

The image conversion at Steps S23 and S28 is not essential, and those steps may be omitted.

After the region extraction is performed on the target image, the controller 11 performs a classification process on the extracted image (segmentation result image) (Step S12 in FIG. 4).

Figure 7:
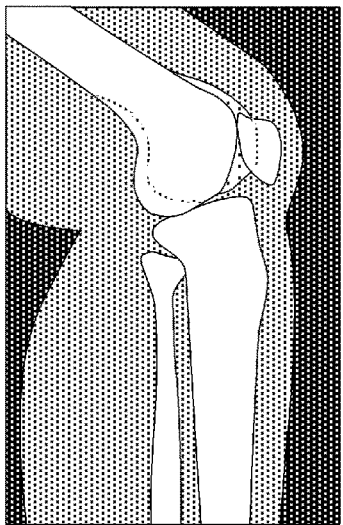
FIG. 7 is an explanatory diagram of a classification process shown in FIG. 4 in detail.
Figure 7:
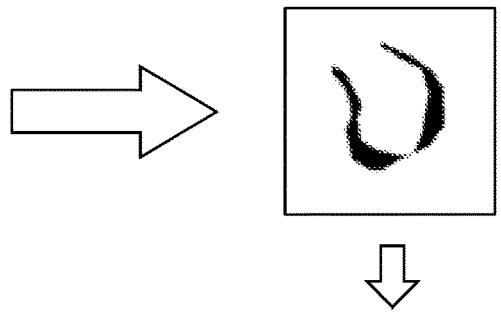
Figure 7:
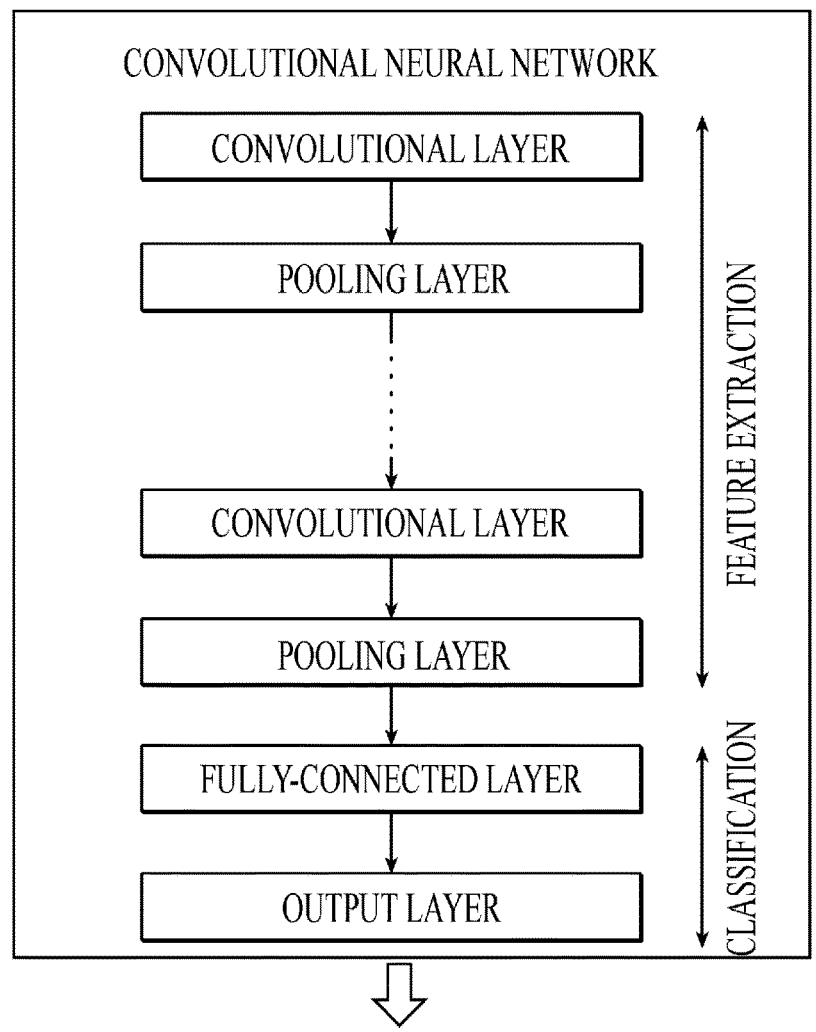

FIG. 7 is an explanatory diagram of the classification process.

As shown in FIG. 7, a convolutional neural network for classification is applied to the segmentation result image extracted from the target image (or the converted image generated by trimming, etc.) by the segmentation process.

The convolutional neural network for classification exemplified in this embodiment classifies the image of the "anatomical structure" (for example, the non-overlapping portion of the medial condyle α and the lateral condyle β) extracted by the segmentation process (the segmentation result image of the target image) into three classes, Classes A, B, and C.

The convolutional neural network for classification is constructed by deep learning similarly to the neural network for segmentation. The neural network used for the classification process is constructed beforehand by deep learning.

Though not shown in the drawings, the controller 11 determines whether the deep learning is completed or not for the convolutional neural network for classification, similarly to the convolutional neural network for segmentation shown in FIG. 5. If the deep learning is not sufficient, multiple sets of training data are prepared and further learned. Those sets of training data (the training data group 12b) are stored in the storage 12, for example.

Figure 8:
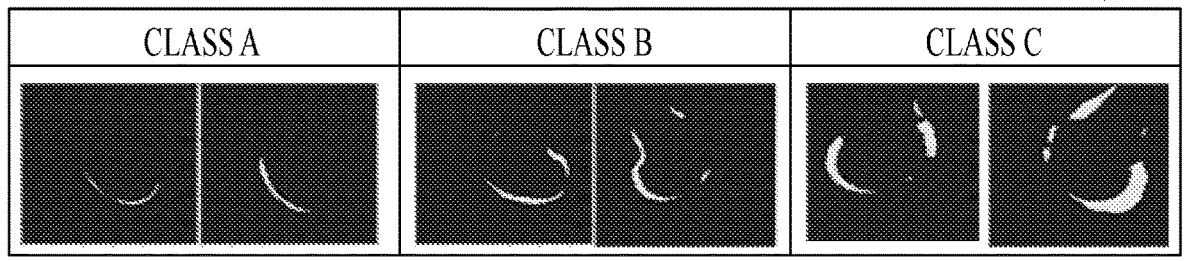
FIG. 8 shows an example of a training data group used in construction of a neural network for classification.

FIG. 8 shows an example of the training data group stored in the storage.

As shown in FIG. 8, the training data group 12b for classification includes segmentation result images (extracted images) of the "anatomical structure" and labeled classes of the segmentation result images respectively associated.

As more sets of data are prepared as the training data group 12b for classification, the effect of the deep learning is enhanced and the accuracy of the constructed neural network is improved. As images taken in various conditions are included in the training data group 12b, it is possible to expect a neural network more robust that enables appropriate classification of various segmentation result images.

The convolutional neural network includes a feature extraction section and a classification section, as shown in FIG. 7.

The feature extraction section, which includes convolutional layers and pooling layers, extracts feature values from the extracted images (the segmentation result images in FIG. 7) generated by the segmentation process. A kernel (filter) is used for convolution so as to extract feature values in the pooling layer. That is, in the pooling layer, the original image (the segmentation result image) is filtered to condense feature points in the concerning image. In the pooling layer, the spatial size of the features is reduced. The structure of the pooling layers and the convolutional layers of the feature extraction section (for example, the number of the convolutional layers and pooling layers, etc.) is not limited and appropriately adjusted.

The classification section, which includes a fully-connected layer and an output layer, expands the values of pixels one-dimensionally in the fully-connected layer, connects units in the fully-connected layer, and then sends them to the output layer.

In the classification section, the segmentation result image is classified into two or more classes on the basis of the feature values extracted in the feature extraction section.

The number of units in the output layer is equal to the number of classes. For example, if a lateral image of the knee is used as in this embodiment, it is equal to the number of levels of an imaging failure of a lateral image of the knee (the levels of, for example: an image involving a complete imaging failure which requires re-imaging; an image involving a slight imaging failure which can be used for diagnosis regardless of a small distortion; and an image not involving an imaging failure, for example). For example, if the segmentation images are classified into three classes, Classes A, B, and C, as in this embodiment, the number of units in the output layer is also three.

The classification in this embodiment involves three classes, but the number of the classes may be two or more, for example, two, four, five, or more.

Parameters of the feature value extraction by the feature extraction section in the convolutional neural network for classification, parameters (weight) of connecting units in the fully-connected layer, etc. are acquired by the deep learning using the training data.

The parameters are updated by repeated learning, and the convolutional neural network for classification is constructed by the parameters updated by the repeated learning.

In the classification section, the level of a non-overlapping portion d of the medial condyle α and the lateral condyle β, the "anatomical structure" (a non-overlapping amount d), etc. is judged and classified, and the judgment result is output as a probability (class score) in the output layer.

For example, shown in FIG. 7 are results of application of the convolutional neural network to the segmentation result image of the target image to be classified, where the probability of Class A is 5%, that of Class B 10%, and that of Class C 85%.

When the judgment process (the positioning judgment process using the machine learning, Step S3 in FIG. 3) is completed, the controller 11 determines whether the judgment result derived using the neural network is that the target image is defective, that is, that re-imaging is necessary due to an imaging failure, as shown in FIG. 3 (Step S4 in FIG. 3).

For example, if classified into Class A, the image can be used as a diagnostic image as an imaging failure is subtle, and the level of the imaging failure gets worse from Class A to Class C. If classified into Class C, the image involves an imaging failure that requires re-imaging. In the case where the classification result is as shown in FIG. 7, the probability of an imaging failure that requires re-imaging is 85%, and thus the controller 11 determines that "the judgment result indicates that the target image is improper".

The reference/threshold value(s) of determination by the controller 11 (for example, classification into which class at what percentage indicates that the judgment result is negative, etc.) may be appropriately set. For example, if a class has the probability (class score) of 80% or more, the image belongs to that class.

If the judgment result indicates that the target image is improper (Step S4; YES), the controller 11 displays a notification of the result of the positioning judgment process (a result display screen 14a in FIG. 9) on the display 14 (Step S5). In that case, the display 14 functions as a result display that displays the judgment results of the convolutional neural network for classification as the judgment unit.

FIG. 9 shows an example of the result display screen of the positioning judgment process.

What to be shown on the result display screen 14a or its layout is not particularly limited, but in FIG. 9, for example, the judgment result of the classification is shown by the probability (class score).

The controller 11 may display the segmentation result image, the extracted image to be the target of the judgment process, on the display 14 (the segmentation display screen 14b in FIG. 10), regardless of whether the judgment result indicates that the target image is improper. In that case, the display 14 displays as the image display that displays the extracted image.

FIG. 10 shows an example of the segmentation display screen.

How to display the segmentation result image on the segmentation display screen 14b is not particularly limited, but in FIG. 10, for example, the segmentation result image (shaded part in the drawing) is superimposed on the target image.

The segmentation result image may be shown alone, but may be comprehended and examined more easily by being superimposed on the target image.

It is not essential to display the result display screen 14a or the segmentation display screen 14b on the display 14. However, as the result display screen 14a and the segmentation display screen 14b are shown on the display 14 to be presented to the user (for example, a doctor or a technician), it is possible to show the certainty of the judgment result of the convolutional neural network for classification as the judgment unit. If a human makes a decision about whether re-imaging is to be performed due to the imaging failure of the target image, such information is useful for the judgment.

If the judgment result by the convolutional neural network for classification as the judgment unit indicating that the target image is improper is displayed on display 14, or if the judgment result by the convolutional neural network for classification as the judgment unit indicates that the target image is not improper (Step S4; NO), the controller 11 requests the user (for example, a doctor or a technician) to check whether the target image is valid ("YES") or invalid ("NO"), and determines whether the user's decision of "YES" or "NO" is input (Step S6).

How to request the user to check the image is not particularly limited, but for example, a "YES button (button to confirm approval of the image)," a "NO button (button to confirm rejection of the image)," or both may be displayed on the display 14, and a message to urge the user to press either button.

If the user does not press any button (Step S6; NO), the controller 11 waits and determines repeatedly whether a decision of "YES" or "NO" is input.

On contrary, if the user presses either button (Step S6; YES), the controller 11 determines whether the user operation is for approval ("YES") (Step S7), and if the decision of "YES" is input (the operation signal indicating "YES" is input, Step S7; YES), the "YES" flag is set ON (the image is flagged by "YES, Step S8). The process is then ended.

If the decision of "NO" (determination that the target image is an imaging failure) is input (an operation signal indicating "NO" is input, Step S7; NO), the "NO" flag is set ON (the image is flagged by "NO", and then the process proceeds to Step 9). The process is then ended.

If the target image is determined to be rejected (that is, the image is flagged by "NO"), the image data of the concerning image may be moved to a specific directory or just deleted.

Alternatively, the decision of approval (YES) may not be actively shown. For example, a rejection button may only be provided, and if the user operation on the rejection button is not input for a predetermined time, it may be determined that "approval" is indicated, and the process may proceed to other steps such as the positioning judgment concerning the next target image, the processing of the next imaging, etc.

The image judgment process as described hereinbefore makes it possible to accurately judge whether the target image is imaged with positioning appropriate as a diagnostic image.

In the image processing device 1 in this embodiment, the controller 11 acquires image data of a medical image that is obtained by radiographing of a part including a region to be diagnosed of a patient, extracts an anatomical structure from the medical image to generate an extracted image (segmentation result image), performs image conversion on the extracted image to generate a converted image, calculates a feature value from the extracted image and/or the converted image by using a result of machine learning, and automatically judges whether the medical image is taken with positioning appropriate for diagnosis based on the feature value by using a result of machine learning concerning feature values.

As described above, a part to be focused on in the judgment is extracted (segmentation) before the judgment of adequacy of positioning. This makes the positioning judgment efficient.

As described above, the segmentation process is performed before the classification process, and the feature extraction and the classification are performed using the machine learning (deep learning) from the segmentation result images. The applications of those processes are not limited to specific cases, and it is possible to effectively judge the adequacy of positioning with a high accuracy even with a small amount of training data.

Further, as the positioning judgment is automated using the machine learning, it is possible to perform a positioning judgment (the judgment of whether the medical image is taken with suitable positioning and appropriate for diagnosis) which may not be easily determined visually.

The machine learning makes it possible to robustly deal with images taken under various conditions.

In this embodiment, in the case where the controller 11 functions as the segmentation unit that generates the segmentation result images, the controller 11 also uses machine learning.

This makes the segmentation highly accurate, making it possible to accurately extract the target of the positioning judgment.

In this embodiment, when the segmentation result image is generated, a processed image that has undergone image processing such as trimming to extract a necessary part from the entire image.

This makes it possible to perform the segmentation process quickly and appropriately.

In this embodiment, the judgment result obtained by applying the neural network for classification is shown as the result display screen 14a on the display 14.

This enables users to easily check the certainty of the judgment process using the neural network.

In this embodiment, the segmentation result image (the extracted image) is displayed on the segmentation display screen 14b of the display 14.

This enables users to easily determine the validity of the target image and easily check the certainty of the judgment process by the neural network.

In this embodiment, a judgment result obtained by using the neural network for classification is classified into two or more classes.

This makes it possible to obtain a result of classification at least concerning whether the medical image to be the target of the judgment involves an imaging failure that requires re-imaging.

The classification into three or more classes as in this embodiment can indicate not only the adequacy of the image but also the level (degree) of the adequacy.

In this embodiment, the medical image to be the target of the judgment is a lateral image of the knee.

In taking a lateral image of the knee, the imaging results significantly differ depending on the incident angle of radiation, the tilting of the target region of the patient, etc. The knee is a region with a complicated structure of joints and bones, and it is difficult to determine whether a medical image of the knee involves an imaging failure.

In this regard, the positioning judgment using the machine learning makes it possible to appropriately determine whether an image of such a complicated region involves an imaging failure.

In the case where the medical image to be the target of positioning judgment is a lateral image of the knee as in this embodiment, the "anatomical structure," which is a point of judgment of an imaging failure, is the medical condyle $\alpha$, the lateral condyle $\beta$, or a non-overlapping portion of the medial condyle $\alpha$ and the lateral condyle on the lateral image of the knee.

This enables an appropriate positioning judgment about images taken under various conditions of, for example, the imaging direction and angle.

Though the embodiment according to the present invention has been described in detail, the present invention is not limited to the above embodiment, and changes can be made within the scope of the present invention.

For example, in the above embodiment, a lateral image of the knee is the medical image to be the target of the positioning judgment, but the medical image to be the target of the positioning judgment is not limited to this.

For example, in FIGS. 11A to 12B, the medical image to be the target of the positioning judgment is a frontal image of the knee.

In the judgment of positioning concerning a frontal image of the knee, the position of the patella (patella b in FIG. 11A) and the appearance of the joint cavity (joint cavity c in FIG. 1A) are important.

An image on which the patella b is positioned in the middle of the knee and the joint cavity c clearly appears without distortion is determined to be an image taken with appropriate positioning.

Thus, when the target of judgment is a frontal image of the knee, the patella b and the joint cavity c are the "anatomical structures," the portions to be the points (to be focused on) of the judgment of an imaging failure.

Figure 11A:
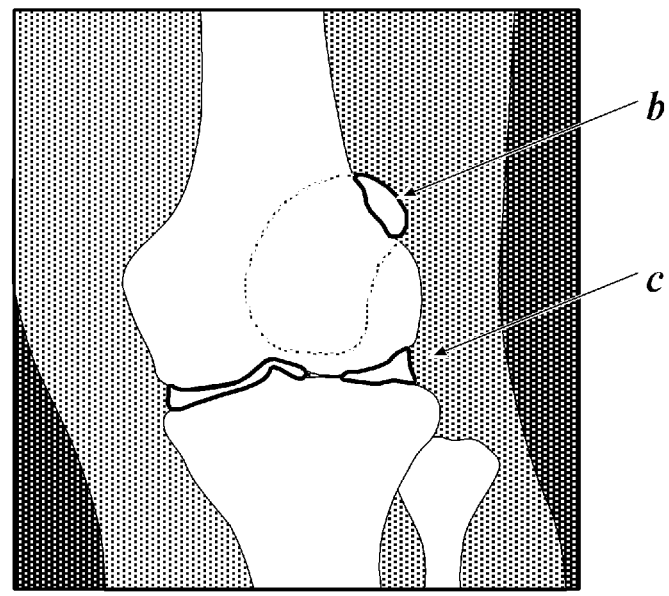
FIG. 11A is a schematic diagram showing an anatomical structure on a frontal image of a knee.

In the case where a region involves multiple "anatomical structures," the segmentation process is performed for each of the points (to be focused on) of the judgment of an imaging failure (the patella b and joint cavity c in the frontal image of the knee shown in FIG. 11A), and the classification process is performed on the basis of the segmentation results of the multiple points.

Figure 11B:
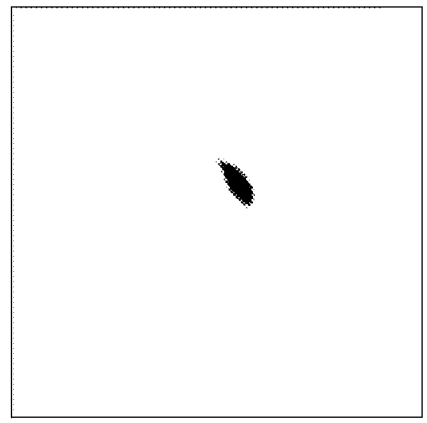
FIG. 11B shows an example of a segmentation result image of apart b shown in FIG. 11A.
Figure 11C:
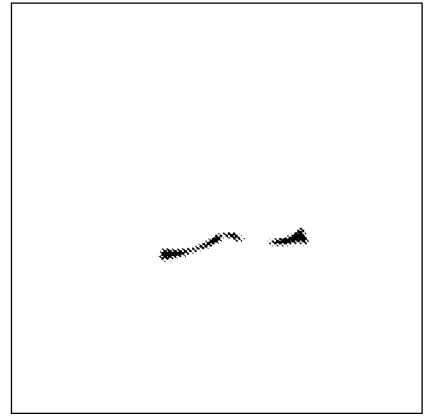
FIG. 11C shows an example of a segmentation result image of apart c in FIG. 11A.

For example, FIG. 11B shows an example of a segmentation result image of the patella b, and FIG. 11C shows an example of a segmentation result image of the joint cavity c.

In that case, the neural network for classification is constructed for each structure (for example, the patella b and the joint cavity c), and the classification process is performed for each structure. The controller 11 then determines whether a target image involves an imaging failure (the adequacy as a diagnostic image) on the basis of the results of the classification process for each structure.

The frontal image of the knee is preferably taken from the front of the region, and an image on which the patella b is positioned in the middle of the knee and the joint cavity c (joint between the upper and lower bones of the knee) clearly appears without distortion is determined to be an image taken with appropriate positioning, as described above.

Figure 12A:
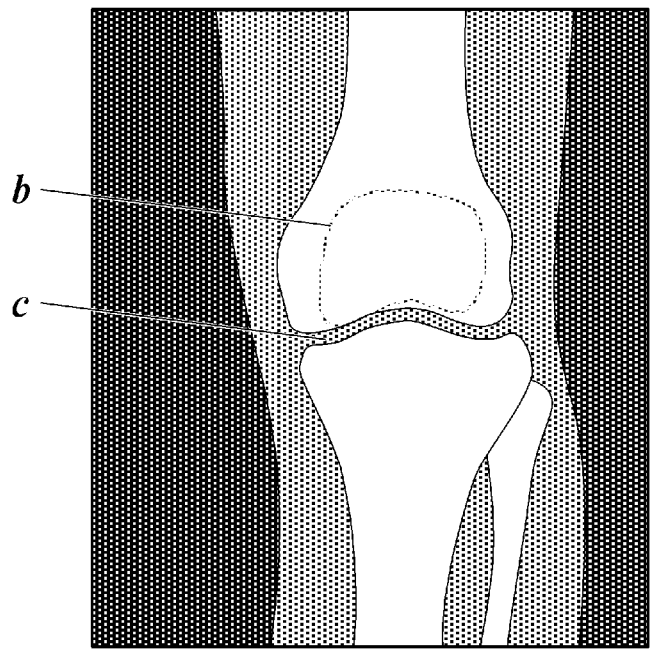
FIG. 12A shows an example of a frontal image of the knee taken with proper positioning.
Figure 12B:
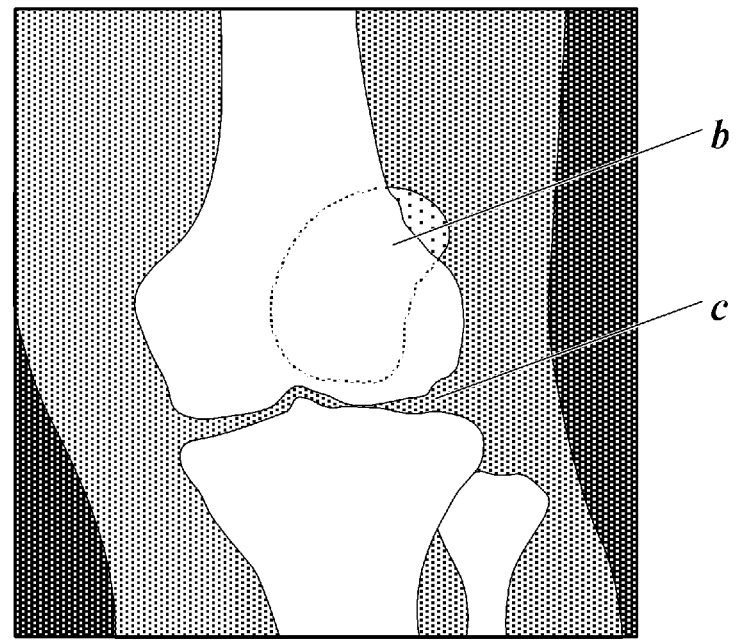
FIG. 12B shows an example of a frontal image of the knee taken with improper positioning.

For example, FIG. 12A shows an example of an image that is determined to be imaged with appropriate positioning. On contrary, FIG. 12B shows an example of an image that is determined to be imaged with improper positioning, in which the patella b is displaced and visible at the back of other bones and part of the joint cavity is distorted. Re-imaging is required in this case due to an imaging failure.

The target image to which the image judgment device, the image judgment method, and the storage medium according to the present invention may be applied is not limited to a lateral or frontal image of the knee. For example, the present invention may be applied to images (medical images) of the upper body such as chest and abdomen or other body parts such as shoulder and arm.

An "anatomical structure" (a portion to be the point (to be focused on) of the judgment of an imaging failure) specific to each part of body is set for each image, and the segmentation process and the classification process are performed for that portion.

This enables an appropriate positioning judgment about images of various parts.

In this embodiment, the image processing device 1 as the image judgment device judges whether a medical image is taken with positioning appropriate for diagnosis, but the judgment by the image processing device 1 is not limited to this example.

The image processing device 1 may judge images about other things than the adequacy of positioning, as long as it extracts a portion (anatomical structure) to be focused on in the judgment of whether the medical image is appropriate for diagnosis in the segmentation process, and judges the adequacy/validity of the image by classification of the extracted image (segmentation result image) using a machine learning method.

The configurations of the convolutional neural networks used in the segmentation process and the classification process are not limited to the examples described in the above embodiment.

For example, the global average pooling to associate one feature map with one class may be used for classification in the feature extraction unit where the feature maps are output as many as the filters. The classification is performed without any fully-connected layer in the classification section in this method.

What is claimed is:

1. An image judgment device, comprising: a hardware processor that functions as:
    an image acquirer that acquires image data of a medical image that is obtained by radiographing a part including a region to be diagnosed of a patient;
    a segmentation unit that extracts an anatomical structure from the medical image to generate an extracted image;
    an image converter that performs image conversion on the extracted image to generate a converted image;
    a feature value extractor that calculates a feature value of the anatomical structure from the extracted image and/or the converted image by using a result of machine learning; and
    a judgment unit that automatically judges whether the medical image is taken with positioning appropriate for diagnosis based on the feature value by using a result of machine learning concerning feature values, wherein a judgment result of the judgment unit is a result of classification of the feature value into three or more classes, wherein each of the classes is associated with a different level of appropriateness of the positioning of the medical image,
    wherein:
    the anatomical structure is a non-overlapping portion between a medial condyle and a lateral condyle in a lateral image of a knee and the feature value is a width of the non-overlapping portion, or
    the anatomical structure is a patella and a joint cavity in a frontal image of a knee and the feature value includes a position of the patella and shape of the joint cavity.

2. The image judgment device according to claim 1, wherein the segmentation unit generates the extracted image by using a result of machine learning.

3. The image judgment device according to claim 1, wherein the hardware processor further functions as an image processor that performs image processing on the image data acquired by the image acquirer so as to generate a processed image, and the segmentation unit generates the extracted image from the processed image.

4. The image judgment device according to claim 1, further comprising: a result display that displays a judgment result of the judgment unit.

5. The image judgment device according to claim 1, further comprising: an image display that displays the extracted image.

6. The image judgment device according to claim 1, wherein the judgement result is output as a probability of each of the classes.

7. The image judgment device according to claim 6, wherein the judgement unit determines that the medical image to one of the classes when the one of the classes has a probability that meets or exceeds a threshold value.

8. The image judgment device according to claim 1, wherein each of the classes is associated with a different level of imaging failure.

9. The image judgment device according to claim 1, wherein the anatomical structure is the non-overlapping portion between the medial condyle and the lateral condyle in the lateral image of the knee and the feature value is the width of the non-overlapping portion.

10. The image judgment device according to claim 1, wherein the anatomical structure is the patella and the joint cavity in the frontal image of the knee and the feature value includes the position of the patella and shape of the joint cavity.

11. The image judgment device according to claim 1, wherein the machine learning is performed by a convolution neural network for segmentation and a convolution neural network for classification.

12. An image judgment method comprising:
    acquiring image data of medical images that are each obtained by radiographing a part including a region to be diagnosed;
    extracting an anatomical structure from each of the medical images to generate extracted images;
    preparing training data by associating the extracted images respectively with adequacy classes of positioning in radiographing the corresponding medical images;
    training a convolutional neural network with the training data so as to set a parameter of the convolutional neural network; and
    acquiring image data of a target medical image that is obtained by actual radiographing of a part including the region to be diagnosed of a patient;
    extracting an anatomical structure from the target medical image to generate an extracted image and calculating a feature value of the anatomical structure in the extracted image; and
    inputting the extracted image and the feature value to the convolutional neural network having the parameter set by the training, and thereby judging as to whether the target medical image was taken with positioning appropriate for diagnosis, wherein a judgment result of the judging is a result of classification of the feature value into three or more classes, wherein each of the classes is associated with a different level of appropriateness of the positioning of the medical image,
    wherein:
    the anatomical structure is a non-overlapping portion between a medial condyle and a lateral condyle in a lateral image of a knee and the feature value is a width of the non-overlapping portion, or
    the anatomical structure is a patella and a joint cavity in a frontal image of a knee and the feature value includes a position of the patella and shape of the joint cavity.

13. A non-transitory recording medium that stores a computer readable program that causes a computer to:
    acquire image data of a medical image that is obtained by radiographing a part including a region to be diagnosed of a patient;
    extract an anatomical structure from the medical image to generate an extracted image;
    perform image conversion on the extracted image to generate a converted image;

calculate a feature value of the anatomical structure from the extracted image and/or the converted image by using a result of machine learning; and automatically judge whether the medical image is taken with positioning appropriate for diagnosis based on the feature value by using a result of machine learning concerning feature values, wherein a judgment result is a result of classification of the feature value into three or more classes, wherein each of the classes is associated with a different level of appropriateness of the positioning of the medical image, wherein:

the anatomical structure is a non-overlapping portion between a medial condyle and a lateral condyle in a lateral image of a knee and the feature value is a width of the non-overlapping portion, or the anatomical structure is a patella and a joint cavity in a frontal image of a knee and the feature value includes a position of the patella and shape of the joint cavity.

* * * * *